United States Patent [19]

Kempe

[11] Patent Number: 5,117,706
[45] Date of Patent: Jun. 2, 1992

[54] BACKLASH-FREE DRIVE FOR THE INFEED MECHANISM OF A MICROTOME

[75] Inventor: Manfred Kempe, Neckargmünd, Fed. Rep. of Germany

[73] Assignee: Cambridge Instruments GmbH, Nussloch Bei Heidelberger, Fed. Rep. of Germany

[21] Appl. No.: 725,781

[22] Filed: Jul. 3, 1991

Related U.S. Application Data

[63] Continuation of Ser. No. 348,578, Apr. 17, 1989, abandoned.

[30] Foreign Application Priority Data

Aug. 21, 1987 [DE] Fed. Rep. of Germany ....... 3727975

[51] Int. Cl.$^5$ ............................................. F16H 55/18
[52] U.S. Cl. ...................................................... 74/441
[58] Field of Search ....................................... 74/441

[56] References Cited

U.S. PATENT DOCUMENTS

| 525,780 | 9/1894 | Boynton | 74/441 |
|---|---|---|---|
| 2,328,732 | 9/1943 | McKinney | 74/441 |
| 2,345,194 | 3/1944 | Granberg et al. | 74/441 |
| 2,690,682 | 10/1954 | Passmann | 74/441 |
| 2,919,596 | 1/1960 | Kuehl | 74/441 |
| 3,001,414 | 9/1961 | Bourne | 74/441 |
| 3,703,835 | 11/1972 | O'Conner et al. | 74/441 |
| 4,114,470 | 9/1978 | Sharpe | 74/441 |
| 4,625,608 | 12/1986 | Behme et al. | 83/713 |

FOREIGN PATENT DOCUMENTS

| 3532895 | 5/1986 | Fed. Rep. of Germany . | |
| 3539138 | 8/1986 | Fed. Rep. of Germany . | |
| 2394724 | 1/1979 | France . | |
| 2132310 | 7/1984 | United Kingdom | 74/441 |
| 2182786 | 5/1987 | United Kingdom . | |

Primary Examiner—Allan D. Herrmann
Assistant Examiner—David W. Laub
Attorney, Agent, or Firm—Bean, Kauffman & Spencer

[57] ABSTRACT

A backlash-free drive for the infeed mechanism of a microtome, comprising a threaded spindle (1) mounted so as to be rotatable but axially non-shiftable, as well as two nut elements (2a, 2b) connected such that they are non-rotatable but can be shifted in an axial direction relative one another, said nut elements being spring-loaded against one another in an axial direction. Acceptable tolerances for the conicity of the threaded spindle are obtained by making use of at least one plain bearing (11,13;12,14) between the threaded spindle and nut element (2a), said nut element being connected to a specimen holder (16) via a gear. Fences (30,32;31,33) acting in the direction of spindle rotation protect the thread from deformation, as do two frictional clutches (24;25), which prevent excessive driving torques from having an effect and allow the user the option of operating the micrometer with manual feed (22) or an automatic feed device (26).

16 Claims, 3 Drawing Sheets

Fig. 1
PRIOR ART
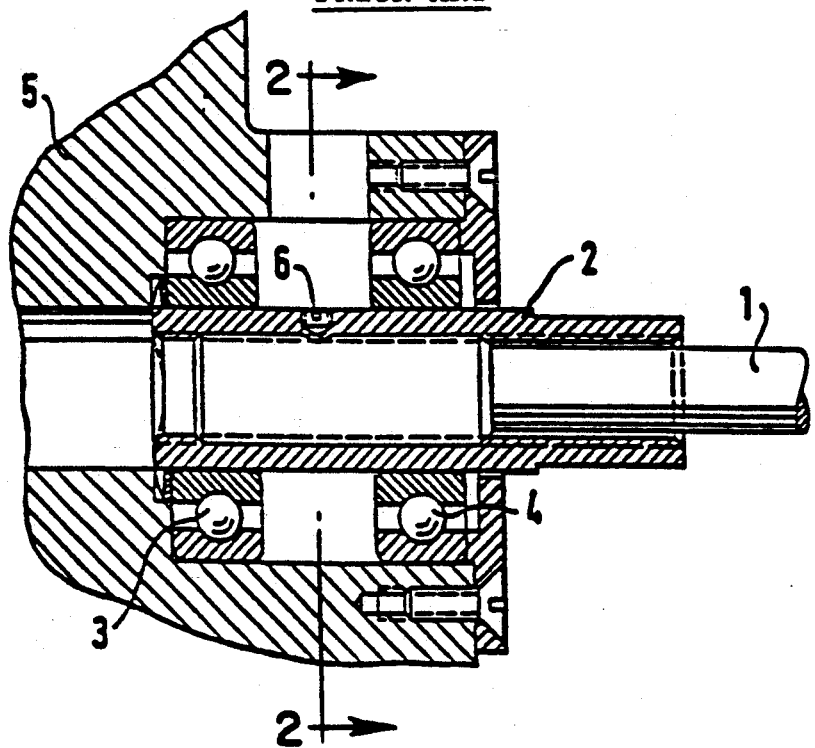
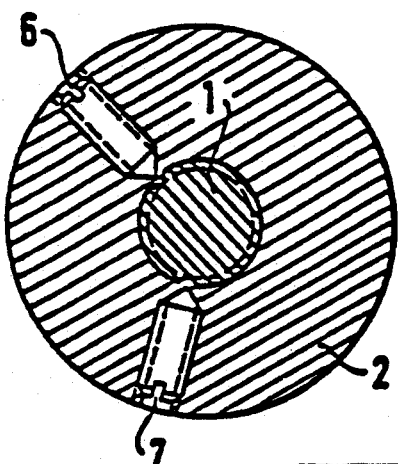
Fig. 2
PRIOR ART

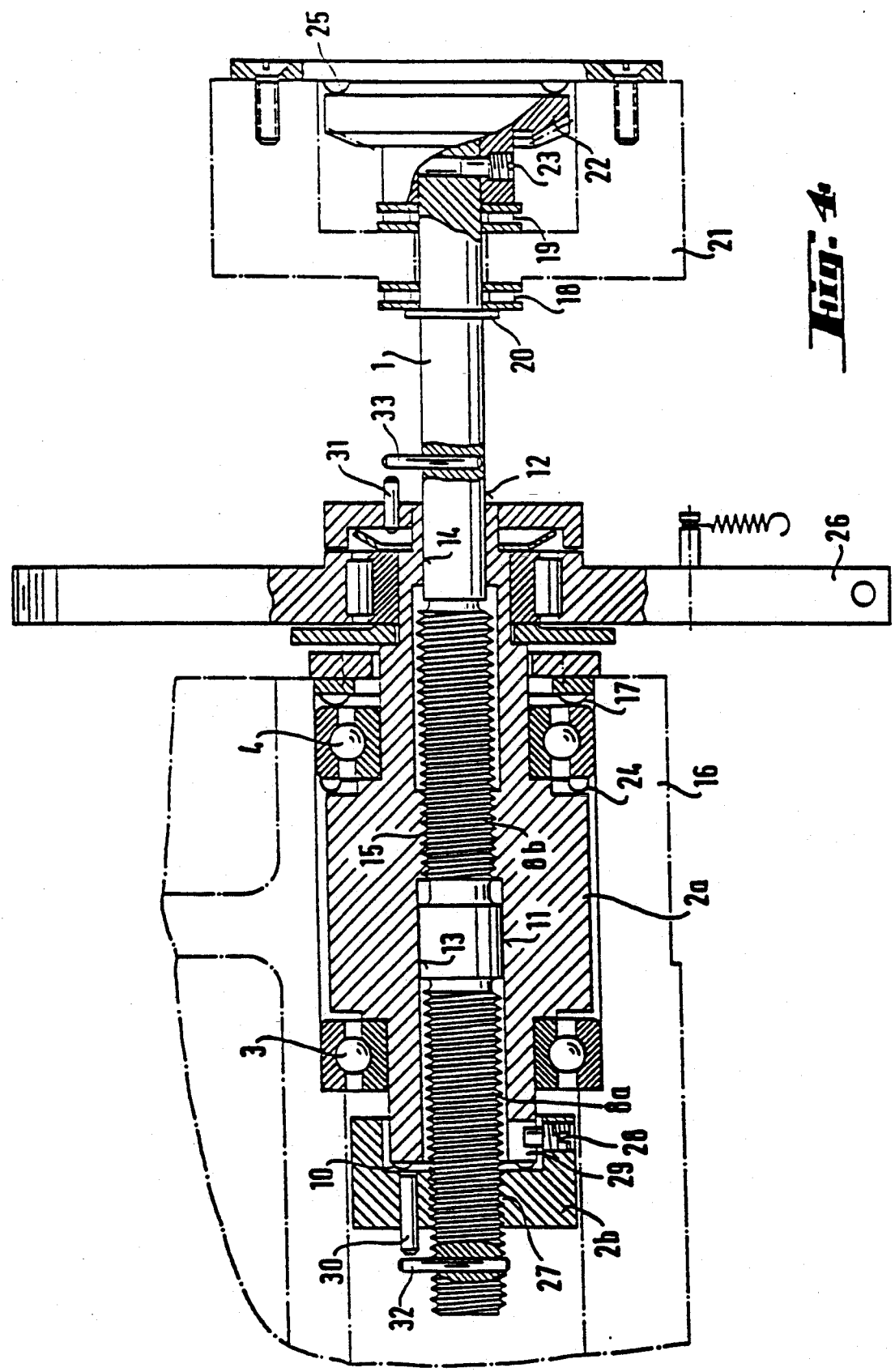

BACKLASH-FREE DRIVE FOR THE INFEED MECHANISM OF A MICROTOME

This is a continuation of copending application Ser. No. 07/348,578 filed on Apr. 17, 1989 now abandoned.

DESCRIPTION

The invention relates to a backlash-free drive for the infeed mechanism of a microtome, comprising a threaded spindle which is mounted so as to be rotatable but not axially shiftable and a spindle nut in cooperation therewith and connected via a gear to a specimen holder which can be infed in the direction of a blade.

A basic requirement for histological examinations is that thickness of cut remain constant. Thickness of cut must remain constant during periods of frequent use of the microtome as well as following lengthy periods of disuse. Ambient temperature should likewise have no effect on thickness of cut. The design and implementation of the infeed mechanism, which is also known as a micrometer mechanism, is of decisive importance in this context. The prior art design employed a screw gear, as shown in FIGS. 1 and 2 for purposes of clarification. This arrangement made use of a two-point or three-point heel acting primarily on the thread crests to prevent axial backlash of threads. However, even slight conicity of the spindle thread renders this point arrangement ineffective, as a result of which incrementation size and hence uniform thickness of cut are no longer ensured; the resulting cuts are thus of varying thickness.

The object of the present invention is to provide a backlash-free drive for the infeed mechanism of a microtome, this mechanism being self-adjusting and to a large extent maintenance-free. According to the invention, this object is fulfilled with the drive described at the outset in that the spindle nut consists of two nut elements which are non-rotatable but can be shifted in an axial direction relative to one another and are spring-loaded against one another. The spring loading of the nut elements is preferably effected by means of a compression spring, in particular, by means of a leaf spring or sinuous spring or at least a helical compression spring. The nut elements are preferably connected to one another in the direction of rotation by means of a pin attached to one of them and engaging in a groove of the other. The resulting precision screw gear is self-adjusting for axial backlash, which occurs when the screw flanks become worn; it ensures reproducible incrementation movements in the $\mu m$ range for feed from the object holding device to the blade and allows greater tolerances in manufacturing.

The connection between the specimen holder and the spindle nut is preferably effected via a nut element by means of two ball bearings spring-loaded against one another by a compression spring. It has been found suitable to provide at least one plain bearing between the screw spindle and the nut element connected via a gear to the specimen holder, with the plain bearing preferably being adjacent to the corresponding nut element. According to a particularly preferred embodiment, a plain bearing is provided on both sides of the thread of the nut element connected via a gear to the specimen holder. This allows stabilized positioning accuracy for radial-axial loads as well as for coarse and fine adjustments, without conicity of the spindle thread leading to problems. It is appropriate for the plain bearings to consist of a cylindrical peripheral piece of the threaded spindle in cooperation with a cylindrical inner wall of the nut element.

In order to avoid damage to the micrometer mechanism, heavy loads must be avoided in the end bearings which restrict feed, and it must be possible to remove the threaded spindle from the end positions without exerting a great deal of force. The invention achieves these objects by restricting the end position for axial movement by means of at least one fence acting in an end area of the spindle nut feed in the direction of spindle circumference. It is appropriate to design this fence such that at least one of the nut elements contains a first fence element on its front end which is disposed away from the other nut element, said fence element engaging after a predetermined number of spindle rotations with a second fence element located on the threaded spindle itself. The thread geometry is thus protected from deformation. A frictional spring-plate clutch protects the micrometer mechanism from excessive driving torque. To this end the nut element fixed to the specimen holder by means of the ball bearings is secured via a first frictional clutch against twisting relative to the specimen holder until a first given torque has been exceeded. The first frictional clutch is preferably a sinuous spring resting against the shoulder of the nut element, said sinuous spring being supported on the outer race of one of the ball bearings. In addition, the threaded spindle is secured via a second frictional clutch against twisting relative to a stationary part of the microtome until a second specified torque has been exceeded.

If a prior art automatic feed device acts on the nut element rotatably mounted at the specimen holder—this automatic feed device rotating against the resistance of the first frictional clutch while the threaded spindle remains motionless under the action of the second frictional clutch—and if the threaded spindle itself is connected to a second feed drive preferably used for rapid feed, with manual drive being suitable, rapid feed and automatic incrementation movement can readily be achieved while simultaneously avoiding the excessive driving torque mentioned above. It has also proven favorable to fix the threaded spindle in an axial direction relative to a stationary part of the microtome by means of at least one needle roller bearing acting in an axial direction. It is preferable to use two needle roller bearings to ensure that the axial mounting of the threaded spindle is free from backlash.

In the following the invention is described in detail with reference to the accompanying drawings.

FIG. 1 shows a longitudinal section of a prior art infeed mechanism of a microtome in which the horizontal feed for the infeed movement between blade and object is effected by means of a screw gear on which the threaded spindle and spindle nut are mated by means of a radial load so as to be nearly free from backlash.

FIG. 2 shows a cross section through the screw gear of the prior art infeed mechanism shown in FIG. 1, with the remaining axial backlash of threads being compensated for by means of radially-disposed functional elements.

FIG. 4 shows a longitudinal section through the infeed mechanism according to the invention, with parts which are not essential for an understanding having been omitted.

Figure 3:
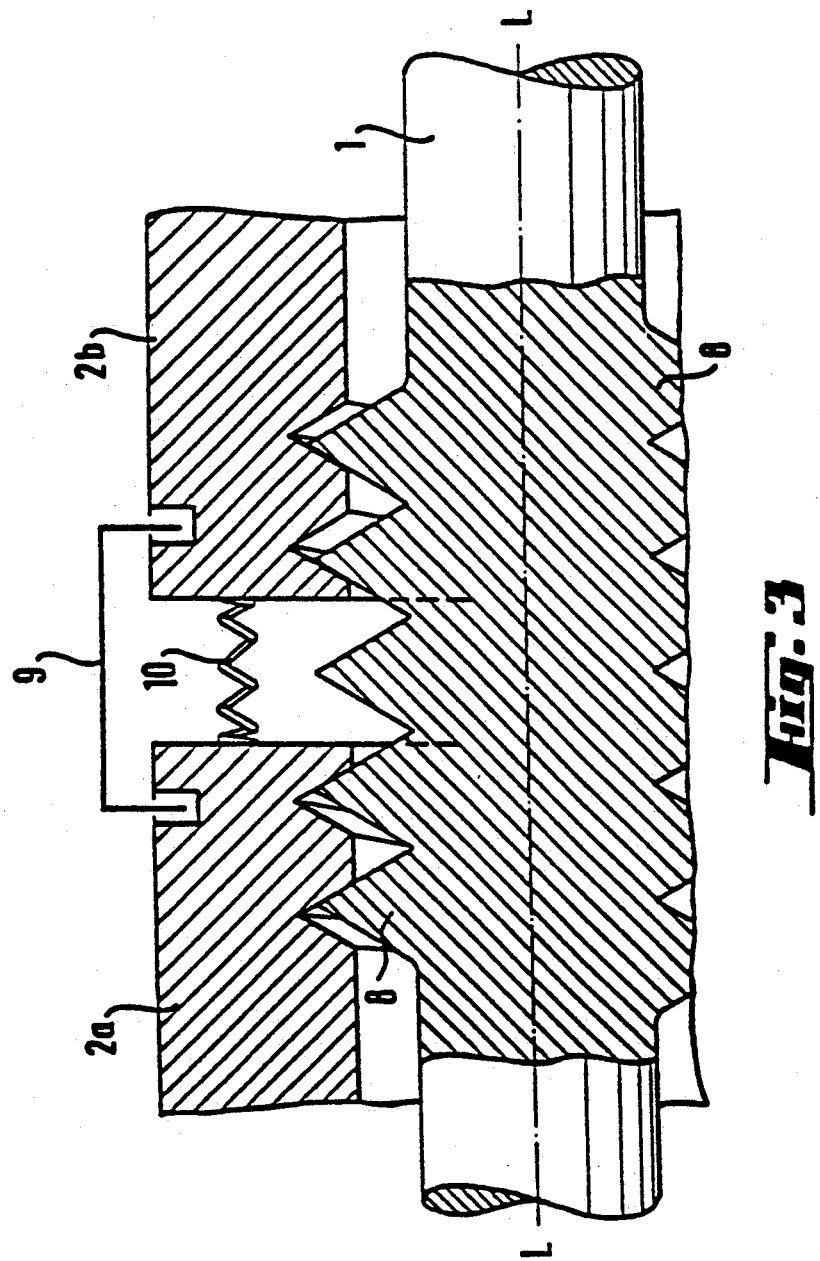
FIG. 3 shows a schematically simplified longitudinal section of an embodiment of a screw gear used for the infeed mechanism according to the invention.

For the prior art infeed mechanism shown in FIGS. 1 and 2, there is provided a threaded spindle 1 to which a spindle nut 2 is attached by means of a threaded joint. Spindle nut 2 is fixed by means of two ball bearings 3, 4 to a specimen holder 5, which is only partially shown, such that the specimen holder is shifted in an axial direction but not rotated when spindle nut 2 is attached at the threaded joint.

In order to eliminate the remaining axial backlash of threads, which is of the magnitude 3–7 μm, radially-disposed functional elements are provided, set screws 6 and 7 in the embodiment shown, thus achieving a two-point or three-point heel acting primarily on the thread crests. Even slight conicity of the spindle gear would render the point arrangement of the radial functional elements ineffective, as a result of which constant feed incrementation could not be guaranteed. Cutting thickness would thus vary, with such variations being highly inappropriate for microtome operation. The design according to the invention, which is shown in FIGS. 3 and 4, provides an infeed mechanism for a microtome whose drive is free from backlash. Essential features of the basic principle involved in this infeed mechanism— which is also referred to as a micrometer mechanism— can be seen in the schematic representation of FIG. 3. The viewer sees threaded spindle 1 in the partially shaded schematic longitudinal section, said threaded spindle being provided in a longitudinal area with a spindle thread 8. Said spindle thread 8 has toothing which is symmetrical relative to a plane extending through the tooth crest and passing vertically through axial direction LL, i.e., a plane extending radially. Together with their respective threads, nut elements 2a and 2b engage with the spindle thread, with nut element 2b serving as lock-nut. As reference number 9 is intended to show, nut elements 2a and 2b are connected to one another so as to be non-rotatable but shiftable in an axial direction relative to one another. Nut elements 2a and 2b are spring-loaded against one another by means of a spring device 10, thus ensuring that nut element 2a and its threads rest against the right tooth flank of the spindle thread, as seen in FIG. 3, while nut element 2b and its threads rest against the left tooth flank of the spindle thread, as seen in FIG. 3, or vice versa, depending on whether spring device 10 acts as a compression spring, as in the case shown, or as a tension spring, as in the other case mentioned.

The arrangement described above results in axial tension between threaded spindle 1 and spindle nut 2, with the nut element which is not connected to the specimen holder, 2a or 2b, acting as a spring-loaded, floatably-mounted lock-nut which compensates for axial backlash of the threads.

This principle of axial tension is also implemented in the concrete embodiment of the infeed mechanism shown in FIG. 4. Portions of spindle nut 1 are provided with a spindle thread 8a or 8b. Spindle nut 1 also contains two precision cylinder guideways 11 and 12, with guideway 11 being located between spindle thread portions 8a and 8b, and guideway 12 being located at the end of spindle 1 disposed towards the infeed mechanism. The diameter of precision cylinder guideway 11 is greater than that of the spindle thread, while that of precision cylinder guideway 12 is smaller than that of the spindle thread, which serves to simplify the assembly of the parts.

Precision cylinder guideways 11 and 12 cooperate with precision cylinder bushes 13, 14, respectively, said precision cylinder bushes being located inside nut element 2a and imparting a centering function to the outer thread diameter of spindle thread 8b, such that any conicity over the length of this thread area 8a has no influence on the constancy of thickness of cut. Thread area 8b of threaded spindle 1 engages with female thread 15 of nut element 2a, such that when threaded spindle 1 rotates, nut element 2a—which is radially mounted via deep-groove ball bearings 3 and 4—shifts the slider 16, which constitutes or supports the specimen holder. Sinuous spring 17 spring-loads the two deep-groove ball bearings 3 and 4 in an axial direction such that a defined radial rotational movement of nut element 2a on threaded spindle 1 takes place without axial shifting relative to mobile slider 16, which transfers the infeed from the object to the blade. Deep-groove ball bearings 3 and 4 are supported axially via spindle 1 on two needle roller bearings 18, 19 to take up axial alternation of load, with the axial needle roller bearings 18, 19 effecting an elimination of backlash.

Needle roller bearing 18 is held against a stationary part of the microtome by a collar 20 of threaded spindle 1 or a snap ring set in a corresponding groove of this spindle. The same applies to needle roller bearing 19, which is held against a stationary part—shown in FIG. 4 as reference number 21—by means of a drive pinion 22 for manual rapid drive attached to the end of threaded spindle 1 or by means of a lock-nut located therebetween which is not shown in the drawings. The drive pinion is held on threaded spindle 1 via a pin 23 or a plate screw so as to be non-rotatable.

Sinuous spring 17 also serves as a countersupport, its spring resistance being selected so as to prevent forward movement of slider 16 during the cutting process, which would pull the object towards the blade. An additional sinuous spring 24, which counteracts sinuous spring 17, is supported on a shoulder of nut element 2a as well as on the outer race of ball bearing 4, thereby forming the first frictional clutch. This clutch prevents nut element 2a from rotating with threaded spindle 1 when threaded spindle 1 is rotated via the drive pinion, thus preventing nut element 2a and the specimen holder from shifting in an axial direction.

A friction disk 25, which serves as a second frictional clutch, rests against the front end of drive pinion 22. Friction disk 25 prevents threaded spindle 1 from rotating when the microtome is switched to "automatic feed", this switching status being effected in what is a prior art technique via an automatic feed device 26 equipped with a ratchet clutch. Automatic feed device 26 acts directly upon nut element 2a and rotates same further by a certain amount for every cut which follows, depending on the desired feed.

As seen in FIG. 4, nut element 2b is screwed on to spindle thread area 8a to the left of nut element 2a and at a distance from same, this being effected by means of female thread 27 of nut element 2b. Nut element 2b is provided with a set screw 28 in its inwardly-directed end, said end area having a reduced outer diameter and overlapping the end area of nut element 2a. This set screw engages in a longitudinal slot 29 extending in an axial direction to threaded spindle 1 on the outer side of nut element 2a. The width of longitudinal slot 29 and the end of set screw 28 projecting into it are measured such that the set screw is positively locked in the longitudinal slot and can be shifted along it. Synchronous action is thus established between nut elements 2a and 2b.

A leaf spring in the form of a sinuous spring or a helical compression spring is provided as spring element 10 between the outwardly-directed front end of nut element 2a and the inwardly-directed front end of nut element 2b. This spring element 10 spring-loads nut elements 2a and 2b against one another as shown more fully in FIG. 3.

The embodiment described above provides a precision screw gear which is self-adjusting with respect to axial backlash and ensures reproducible incrementation movements in the μm range between the blade, which is not shown, and the object holding device when the thread flanks show signs of wear.

By virtue of the synchronous action of nut elements 2a and 2b, the entire length of the threaded spindle can be exploited. Furthermore, greater manufacturing tolerances can be permitted for the threaded spindle and the threads of the spindle nuts, which renders the manufacture of the entire infeed mechanism more economical.

Protruding fence elements are also provided on the front ends of nut elements 2a and 2b disposed away from one another, these elements comprising pins 30 and 31, respectively, in FIG. 4. These fence elements cooperate with fence elements 32 and 33, which are located on the front and rear areas of the threaded spindle, respectively, and comprise pins passing through threaded spindle 1 and protruding beyond its circumference. After a predetermined number of spindle rotations in a "forward direction", fence elements 30 and 32 meet in the circumferential direction. The furthest position to which nut elements 2a and 2b can be returned is restricted by fence elements 31 and 33, which likewise meet in the circumferencial direction. As soon as this takes place, an arrest is effected between the threaded spindle and spindle nut 2, such that for further rotary movements caused by a driving torque the spindle nut rotates synchronously with threaded spindle 1, thereby rendering it impossible for spindle nut 2 to be tightened against threaded spindle 1 or a part of the casing. This prevents deformation of the thread flanks as well as extension of the thread shaft. Thread pitch thus remains constant over the entire length of the thread, which is of great importance for exact infeed.

In summary, it can be said that the drive for an infeed mechanism described above allows greater precision while simultaneously reducing manufacturing, assembly, and service costs.

I claim:

1. A microtome having a backlash-free drive for the infeed mechanism, comprising a threaded spindle which is mounted so as to be rotatable but axially non-shiftable and a gear-driven spindle nut in cooperation with said spindle, said spindle nut being rotatably connected to a specimen holder which can be infed in the direction of a blade, characterized in that the spindle nut consists of two nut elements (2a, 2b) which are locked together for rotation and can be shifted relative to one another in an axial direction, said nut elements being rotatably connected to a specimen holder (16) by means of two shared ball bearings (3,4) and spring-loaded relative to one another in an axial direction.

2. Drive as claimed in claim 1, characterized in that the spring loading of the nut elements (2a, 2b) is effected by means of a compression spring (10), whereby said compression spring is leaf, sinuous, or helical.

3. Drive as claimed in claim 1, characterized in that the two nut elements (2a, 2b) are connected to one another in the direction of rotation by means of a pin (28) which is attached to one of the nut elements and engages in a groove (29) of the other.

4. Drive as claimed in claim 1, characterized in that at least one plain bearing (11,13;12,14) is provided between threaded spindle (1) and nut element (2a) which is connected via a gear to specimen holder (16).

5. Drive as claimed in claim 4, characterized in that plain bearing (11,13) is located adjacent to the thread (15) of nut element (2a) connected via a gear to specimen holder (16).

6. Drive as claimed in claim 5, characterized in that a plain bearing (11, 13; 12, 14) is provided on each side of thread (15) of nut element (2a) connected via a gear to specimen holder (16).

7. Drive as claimed in claim 4, characterized in that the plain bearing is formed of a cylindrical peripheral piece (11, 12) of the threaded spindle and a cylindrical inner wall (13, 14) of nut element (2a).

8. Drive as claimed in claim 1, characterized in that there is provided at least one fence (30,32; 31,33) acting in an end area of the spindle nut feed in the direction of spindle rotation.

9. Drive as claimed in claim 8, characterized in that at least one of the nut elements (2a, 2b) contains a first fence element (30, 31) on its front end disposed away from the other nut element (2a, 2b), said fence element engaging after a predetermined number of spindle rotations with a second fence element (32, 33) provided on threaded spindle (1) itself.

10. Drive as claimed in claim 1, characterized in that nut element (2a), which is mounted to specimen holder (16) by means of ball bearings (3, 4), is secured via a first frictional clutch against twisting relative to specimen holder (16) until a first given torque has been exceeded.

11. Drive as claimed in claim 10, characterized in that the first frictional clutch is a sinuous spring (24) resting against a shoulder of nut element (2a), said sinuous spring (24) being supported on the outer race of one of the two ball bearings (4).

12. Drive as claimed in claim 1, characterized in that threaded spindle (1) is secured via a second frictional clutch (25) against twisting relative to a stationary part (21) of the microtome until a second given torque has been exceeded.

13. Drive as claimed in claim 11, characterized in that a prior art automatic feed device (26) acts upon nut element (2a), which is rotatably mounted in specimen holder (16), said automatic feed device turning nut element (2a) against the resistance of the first frictional clutch while threaded spindle (1) remains stationary under the action of the second frictional clutch (25), and in that threaded spindle (1) is connected via a gear to a second feed drive (23) which is preferably used for rapid feed.

14. Drive as claimed in claim 1, characterized in that threaded spindle (1) is held in an axial direction relative to a stationary part (21) of the microtome by at least one needle roller bearing (18, 19) acting in an axial direction.

15. Drive as claimed in claim 14, characterized in that two needle roller bearings (18, 19) are used to ensure a backlash-free axial mounting of threaded spindle (1).

16. A microtome having a backlash-free drive for the infeed mechanism, comprising a threaded spindle which is mounted so as to be rotatable but axially non-shiftable and a gear-driven spindle nut in cooperation with said spindle, said spindle nut being connected to a specimen holder which can be infed in the direction of a blade, wherein the spindle nut consists of two nut elements (2a, 2b) which are non-rotatable relative to each other and can be shifted relative to one another in an axial direction, said nut elements being spring-loaded against one another in an axial direction characterized in that each of said nut elements (2a, 2b) is rotatably connected to the specimen holder (16) by means of two shared ball bearings (3, 4) which are spring-loaded toward one another with compression springs (10, 17) and rotatably connected to spindle (1) by a plane bearing (11, 13; 12, 14).

* * * * *